US005662835A

United States Patent [19]
Collingwood

[11] Patent Number: 5,662,835
[45] Date of Patent: Sep. 2, 1997

[54] APPARATUS FOR EMANATING A CHEMICAL AGENT

[75] Inventor: Keith Collingwood, Hull, England

[73] Assignee: Reckitt & Colman Products Limited, London, England

[21] Appl. No.: 607,422

[22] Filed: Feb. 28, 1996

[30] Foreign Application Priority Data

Mar. 4, 1995 [GB] United Kingdom .................. 9504359

[51] Int. Cl.⁶ ........................................ B01F 3/04
[52] U.S. Cl. .................. 261/26; 261/30; 261/DIG. 65; 261/99; 239/45; 239/47
[58] Field of Search .................. 261/99, 30, DIG. 65, 261/26; 239/45, 47

[56] References Cited

U.S. PATENT DOCUMENTS

| | | | |
|---|---|---|---|
| 4,035,451 | 7/1977 | Tringali | 261/DIG. 65 |
| 4,878,615 | 11/1989 | Losi | 239/45 |
| 5,060,858 | 10/1991 | Santini | 261/DIG. 65 |
| 5,242,111 | 9/1993 | Nakoneczyn et al. | 239/47 |
| 5,250,265 | 10/1993 | Kawaguchi et al. | 422/124 |
| 5,282,571 | 2/1994 | Smith et al. | 261/DIG. 65 |
| 5,431,885 | 7/1995 | Zlotnik et al. | 422/124 |

*Primary Examiner*—Tim R. Miles
*Attorney, Agent, or Firm*—Frederick H. Rabin

[57] ABSTRACT

An apparatus for emitting a chemical agent includes a supply of the chemical agent, an emanator from which the chemical agent can diffuse, means for transporting the chemical agent from the supply to the emanator, means for interrupting the transportation of the chemical agent from the supply to the emanator and means for providing a flow of air over the emanator to promote diffusion of the chemical agent from the emanator. The supply of the chemical agent, the emanator, the means for transporting the chemical agent and the means for interrupting the transportation of the chemical agent may be provided in the form of an integral replaceable cartridge.

18 Claims, 3 Drawing Sheets

APPARATUS FOR EMANATING A CHEMICAL AGENT

This application relates to apparatus for emitting a chemical agent, and in particular for emitting a chemical agent such as a fragrance or insecticide.

Many types of apparatus for emitting a chemical agent are known including, for example, those in which the chemical agent is contained in a gel material from which the chemical agent is able to diffuse into the atmosphere. Devices of this type have the disadvantage that it can be difficult to control the rate of diffusion of the chemical agent, that the rate of diffusion is insufficient or that the rate of diffusion decreases with time. Devices are also known in which heat is applied to the chemical agent in order to increase the rate of diffusion of the chemical agent.

The present invention therefore seeks to provide an apparatus for emitting a chemical agent which can overcome the above and other disadvantages, by emitting the chemical agent controllably, at a preset level and preferably at a substantially constant rate of diffusion during the period of its operation in which the apparatus emits the chemical agent. Desirably, the apparatus is adapted to emit the chemical agent intermittently.

It is further desirable to provide means for replacing or replenishing the supply of the chemical agent.

Accordingly, a first aspect of the present invention provides an apparatus for emitting a chemical agent comprising:
a supply of the chemical agent, an emanator from which the chemical agent can diffuse, means for transporting the chemical agent from the supply to the emanator, means for interrupting the transportation of the chemical agent from the supply to the emanator, and means for providing a flow of air over the emanator to promote the diffusion of the chemical agent from the emanator.

After operation of the apparatus of the invention for a period of time, the supply of chemical agent will become exhausted and the efficiency of the emanator can be reduced, for example because of the deposition in the emanator of non-volatile components of the chemical agent. Similarly, the efficiency of the means for transporting the chemical agent can decrease with time.

In a preferred embodiment of the invention, the emanator, the supply of the chemical agent and the means for transporting the chemical agent from the supply to the emanator are in the form of an integral replaceable cartridge. In a preferred variation of this embodiment, the emanator is moveably attached to the main body of the cartridge and may be moved between a first position in which the emanator is in communication with the means for transporting the chemical agent and a second position in which communication with the means for transporting the chemical agent is broken.

According to a second aspect of the invention there is provided an integral cartridge adapted to be replaceably incorporated in an apparatus for emitting a chemical agent, the cartridge comprising a supply of the chemical agent, an emanator from which the chemical agent can diffuse, means for transporting the chemical agent from the supply to the emanator and means for interrupting the transportation of the chemical agent from the supply to the emanator.

In a particularly preferred variation of the invention, the emanator is moveably attached to the main body of the cartridge and may be moved between a first position in which the emanator is in communication with the means for transporting the chemical agent and a second position in which communication with the means for transporting the chemical agent is broken.

In this manner, when the apparatus or cartridge is not in use, the communication between the emanator and the supply of chemical agent can be interrupted so that diffusion of the chemical agent which might undesirably occur is prevented. This construction is also advantageous where it is desired to use the apparatus of the invention to emit a plurality of chemical agents. Thus, a first cartridge including a first emanator can be provided with a supply of a first chemical agent, such as a first fragrance. After a period of use, the first cartridge and its associated emanator can be removed from the apparatus and replaced by a second cartridge including a second emanator and a supply of a second chemical agent such as a second fragrance.

In one preferred form of the invention, the chemical agent is a liquid and the means for transporting the chemical agent is a capillary device such as a wick which is in communication at a first portion thereof with the chemical agent and at another portion thereof with the emanator. In this form of the invention, the means for interrupting the transportation of the chemical agent desirably comprises means for preventing flow of the chemical agent from the supply or from the capillary device to the emanator.

Preferably, the emanator comprises a porous material, preferably a self supporting porous material and particularly preferably a sintered polypropylene or sintered polyethylene material.

In an advantageous construction, the surface area of the emanator is increased by including therein hollow portions, voids, slots or bores open to the atmosphere or by otherwise providing the emanator with a convoluted surface. Thereby, the efficiency of diffusion of the chemical agent from the emanator is increased.

The means for providing a flow of air over the emanator may simply be the provision of apertures, such as ventilation apertures, in the casing of the device, to allow a natural flow of air currents over the emanator.

However, in a particularly preferred form of the apparatus of the invention, the means for providing a flow of air over the emanator comprises an electrically operable fan. Desirably, the apparatus of the invention includes a timer device whereby the fan can be caused to operate intermittently. It is, for example, particularly desirable when the chemical agent is a fragrance material for the fan to operate for approximately three minutes in every twelve to fifteen minutes.

In still another preferred form of the invention, the fan is driven by an electric motor which derives its power from electric cells (batteries). These batteries will also, in time, become exhausted. It is therefore desirable that simple means are provided whereby the batteries can be replaced.

Optionally, the cartridge may include a first compartment comprising a reservoir for the chemical agent and containing at least a portion of the capillary device and a second compartment containing, or adapted to contain, the electric cells.

A series of cartridges containing different chemical agents may be provided so that a user can select a cartridge containing a desired chemical agent and insert the same into the apparatus of the invention.

Preferably, the emanator includes a formation by means of which formation communication is established with the means for transporting the chemical agent. Where the means for transporting the chemical agent is a capillary device, the formation preferably penetrates an end portion of the capillary device when the emanator is in its first position. Particularly preferably, the capillary device comprises a material which is sufficiently resilient to regain, at least in part, its original shape when the formation is removed therefrom, that is, when the emanator is moved to its second position.

In a further preferred construction, the supply of chemical agent (reservoir) initially includes a breakable seal portion which can be broken by, for example, the formation provided on the emanator when the emanator is moved to its first position.

In another preferred construction, the capillary device may be contained within the first compartment of the cartridge and the breakable seal portion is in juxtaposition with an end portion of the capillary device. Thus, on breaking the seal portion, the formation of the emanator enters into communication with the capillary device.

In another preferred variation of the invention, the apparatus includes electric terminals adapted to cooperate with terminals on the second compartment in electrical connection with the electric cells. Alternatively, the second compartment may be so constructed that the terminals of the cells may cooperate directly with the terminals of the apparatus. Electric current can thereby pass through the terminals of the apparatus via a control means (such as, for example, a switch and/or a timer control circuit) to drive the electric motor associated with the fan.

For a better understanding of the invention and to show how the same may be carried into effect, reference will now be made, by way of example only, to the following drawings, in which.

Figure 1:
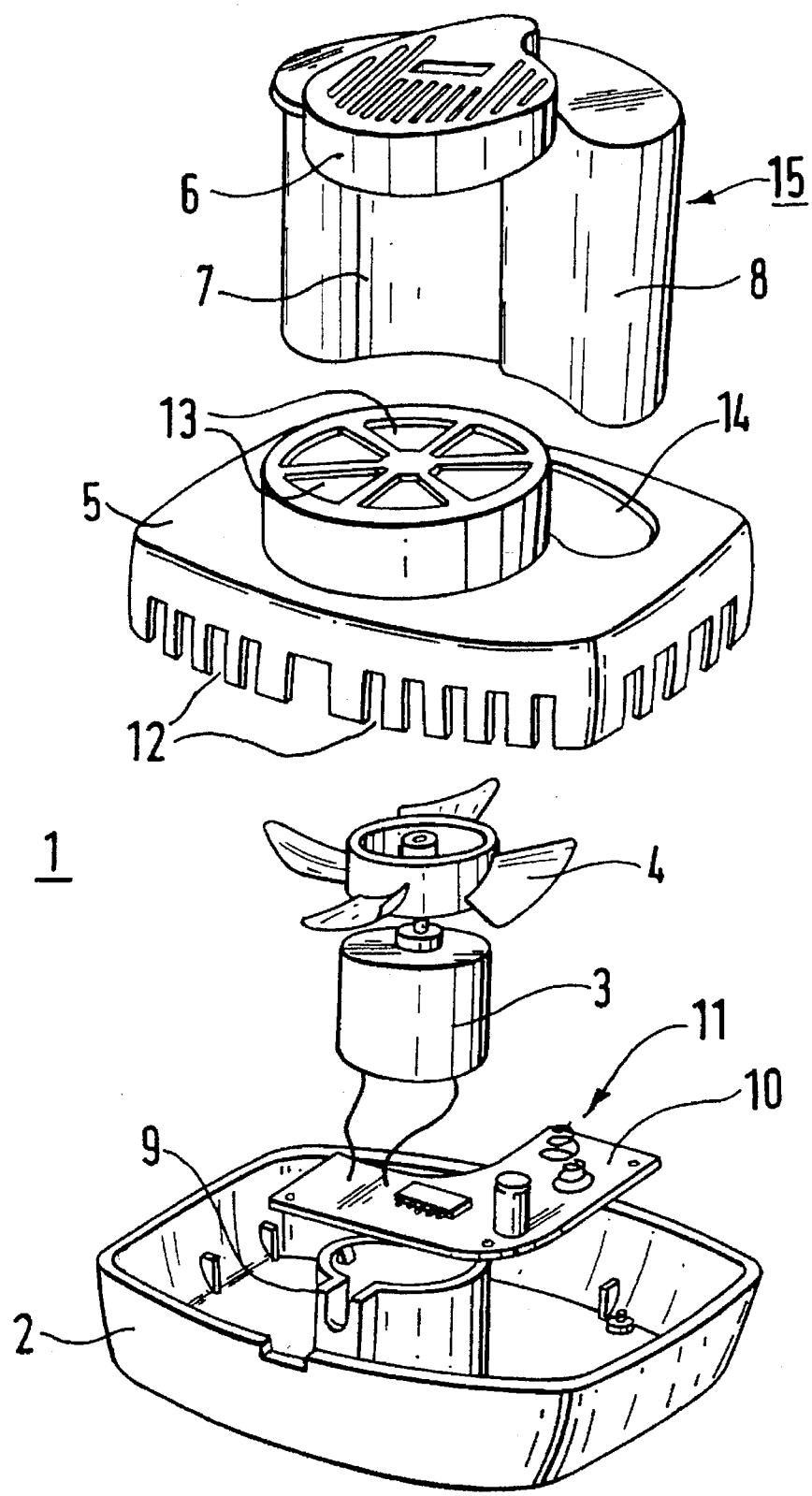
FIG. 1 is an exploded view of the apparatus of the invention illustrating the principal components.

Referring now to the drawings, the apparatus 1 includes a base portion 2, an electric motor 3, a fan 4 driven by the motor 3, a cover or partition 5, an emanator 6, a reservoir 7 for the chemical agent and a compartment 8 for the electric cells. The motor 3 is mounted in a motor housing 9 in the base portion 2. The base portion 2 also includes a circuit board 10 on which electric contacts 11 for the electric cells may be mounted. The circuit board 10 may also include control means such as switches and timer circuits. The cover 5 prevents access to the motor 3, fan 4 and associated components after manufacture and includes cut-outs or vents 12, 13 for the passage of air. Cover 5 also includes a recess 14 adapted to receive the cartridge 15. The apparatus 1 also includes a vented protective cover (not illustrated) adapted to mate with the base portion 2.

In the illustrated embodiments the cartridge 15 includes the emanator 6, the reservoir 7 and the battery compartment 8 as an integral unit. It will be appreciated, however, that other constructions of the cartridge are within the scope of the invention and, in particular, it is not essential for the battery compartment 8 to be an integral part of the cartridge 15.

Figure 4:
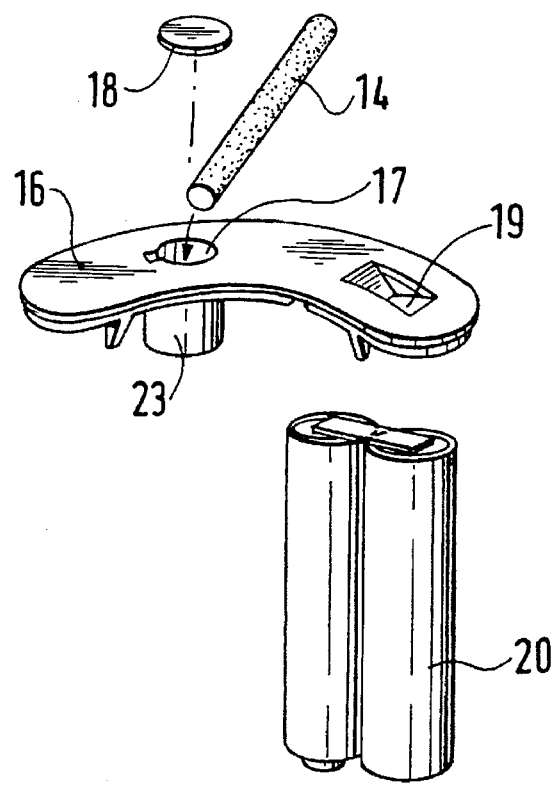
FIG. 4 is an exploded view of a variation of the cartridge of FIGS. 2 and 3 showing the principal components. For reasons of clarity, the emanator is not shown.
Figure 4:
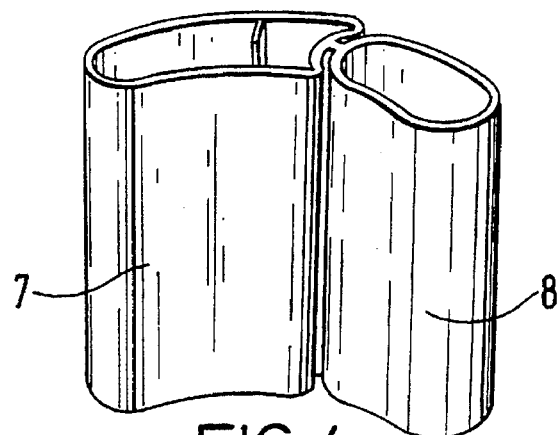

As can particularly be seen from FIG. 4 the means for transporting the chemical agent comprises a wick 14 which is held in position by a guide 23. The wick is thus in fluid communication with the chemical agent in the reservoir 7. Suitable materials for the wick include materials derived from polypropylene fibres, polyethylene fibres, cellulose acetate fibres or polyester fibres. The guide 23 is desirably formed integrally with a closure 16 for the reservoir 7 and, if present, for the compartment 8.

A through hole 17 is provided in the closure 16 in alignment with the end of the wick 14. The hole 17 is desirably initially sealed by means of breakable or removable sealing member 18. The closure 16 may include a biasing means 19 to urge the electric cells 20 onto electric terminals in the compartment 8 or onto the terminals 11 of the circuit board 10.

In the illustrated embodiments, the emanator 6 is formed from a sintered polypropylene material or a sintered polyethylene material and includes a plurality of slots 21 in order to increase its surface area and to provide for the through flow of air from the fan 4. As can be seen from FIG. 1, in use, the cartridge 15 is received in the recess 14 so that the emanator 6 is in juxtaposition with the vents 13 above the fan 4. The chemical agent is transported from the reservoir 7 to the emanator 6 by means of the wick 14.

The chemical agent is carried from the wick 14 by capillary action into the pores of the emanator 6. When the fan 4 is in operation, the flow of air over the surfaces of the emanator 6 greatly increases the rate of evaporation of the chemical agent from the emanator 6, so that the chemical agent diffuses into the surrounding atmosphere.

Figure 2:
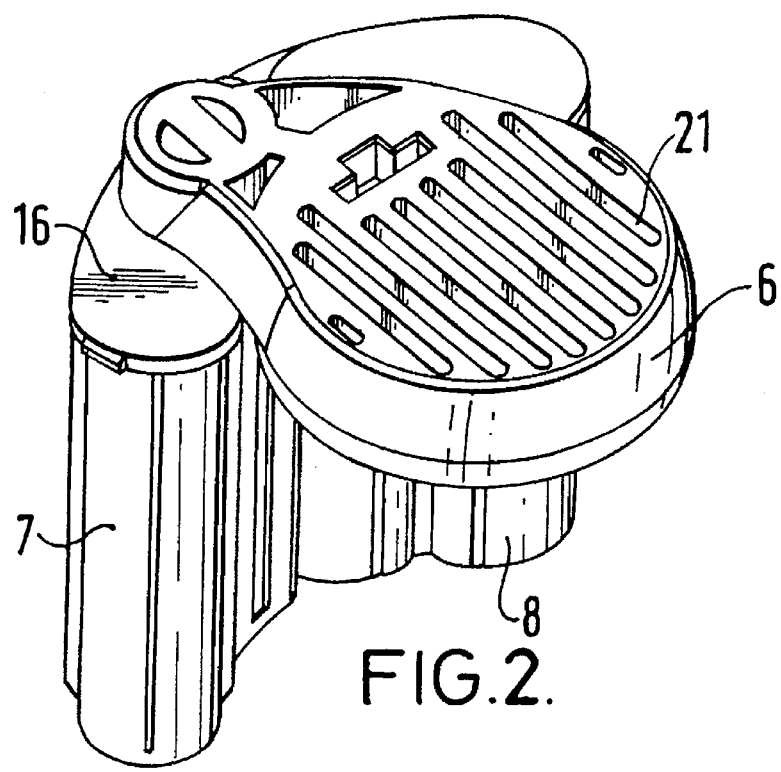
FIGS. 2 and 3 are views of one form of the cartridge of the invention respectively in the first and second positions.
Figure 3:
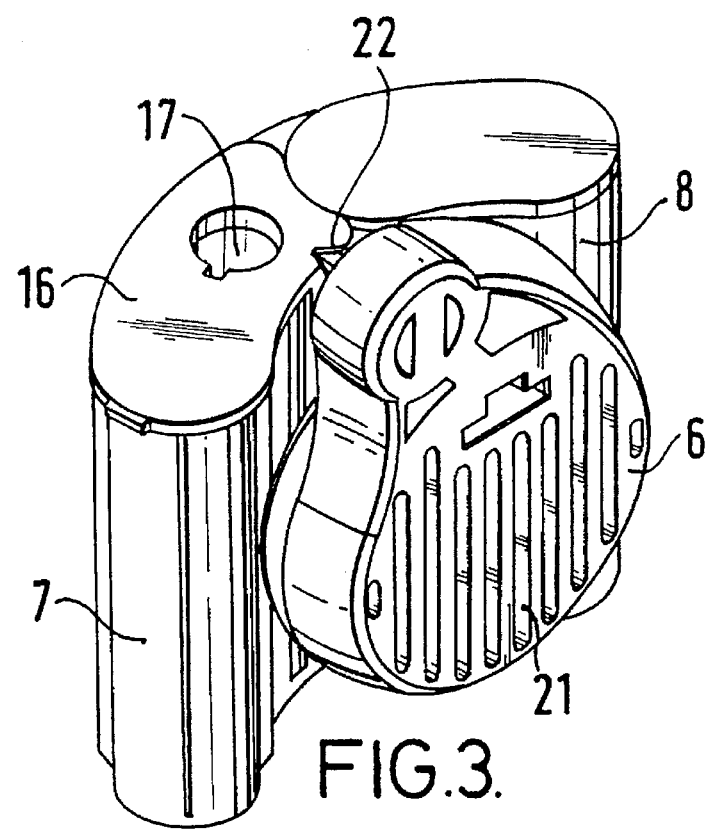

The emanator 6 is pivotally attached to the main body of the cartridge 15 by means of a hinge so that the emanator can be moved between the first position illustrated in FIG. 2 and the second position illustrated in FIG. 3. Any suitable hinge may be employed, such as, for example, a film hinge of a plastics material. It will be appreciated that the emanator may be moved between first and second positions by other suitable means. For example, the emanator may be slidably attached to the main body of the cartridge. However, the hinged construction is advantageous in that when the emanator is in the second position, the cartridge as a whole occupies a minimum of space.

Figure 5:
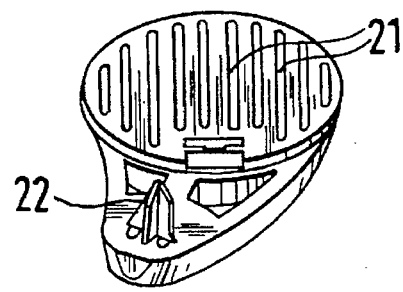
FIG. 5 is a view of the emanator of FIGS. 2 and 3 showing formation 22.

The emanator 6 includes a formation 22 (which is shown most clearly in FIG. 5, and is also shown in FIG. 3) which, when the emanator 6 is in its first position, is in communication with the wick 14 through the hole 17. In this first position, the chemical agent may be transported from the reservoir 7 to the emanator 6 via the wick 14 and the formation 22. In the second position the formation 22 is spaced from the wick 14 and transfer of the chemical agent from the reservoir 7 to the emanator 6 is not possible.

In use, the cartridge 15 is initially supplied with the emanator in its second position and with the hole 17 sealed by the sealing member 18. The emanator 6 can then be moved from the second position to the first position so that the formation 22 breaks the seal member 18 and moves into communication with the wick 14. Means may be provided, such as a snap-locking detent, to retain the emanator in the first position.

After a period of use of the apparatus, the supply of the chemical agent will be exhausted and the electric cells 20 will also become exhausted. Desirably, the electric cells 20 are selected so that they become exhausted after the supply of chemical agent has become exhausted. When the supply of chemical agent is exhausted, the cartridge 15 including the emanator 6 can simply be removed and replaced with a new cartridge 15 containing a new supply of the chemical agent and, optionally, new electric cells 20.

A particular feature of the apparatus of the invention is that a plurality of cartridges 15 may be provided each containing a different chemical agent, such as different fragrances. Thus, the user may choose a desired fragrance by selecting the cartridge containing that fragrance and inserting the same in the apparatus of the invention. An alternative fragrance may be selected by removing the cartridge from the apparatus and inserting a new cartridge containing the alternative fragrance in the reservoir 7. On removal of the cartridge 15 from the apparatus 1, the emanator 6 is preferably moved from the first position to the second position so that further diffusion of the fragrance is prevented.

The cartridges may, of course, be removed from, and replaced in the apparatus as desired by the user until the supply of fragrance is exhausted. In order to prevent evaporation of the chemical agent from the hole 17 (after the sealing member 18 is broken) when the emanator 6 is in the second position, an additional closure (not illustrated) for hole 17 may be provided.

I claim:

1. Apparatus for emitting a volatile chemical agent comprising:
   a supply of the chemical agent;
   a movable emanator from which the chemical agent can diffuse;
   means for transporting the chemical agent from the supply to the emanator;
   means for interrupting the transportation of the chemical agent from the supply to the emanator; and
   means for providing a flow of air over the emanator to promote the diffusion of the chemical agent from said emanator;
   said emanator being adapted to move between a first position in which the emanator is in communication with the means for transporting the chemical agent and a second position in which the communication is interrupted.

2. An integral cartridge adapted to be replaceably incorporated in an apparatus for emitting a chemical agent, which cartridge comprises:
   a main body including a first compartment comprising a reservoir for the chemical agent;
   an emanator from which the chemical agent can diffuse;
   means for transporting the chemical agent from the reservoir to the emanator; and
   means for interrupting the transportation of the chemical agent to the emanator;
   said emanator being movably attached to said main body and adapted to move between a first position in which the emanator is in communication with the means for transporting the chemical agent and a second position in which the communication is interrupted.

3. A cartridge according to claim 2 in which the main body includes a second compartment containing, or adapted to contain, electric cells for operating a fan which provides for a flow of air over the emanator.

4. A cartridge according to claim 2 wherein the chemical agent is a liquid and the means for transporting said chemical agent is a capillary device which is in communication at a first portion thereof with said chemical agent and at another portion thereof with the emanator.

5. A cartridge according to claim 4 wherein the capillary device is a wick.

6. A cartridge according to claim 5 wherein the means for interrupting the transportation of the chemical agent comprises means for preventing flow of said chemical agent from the reservoir or from the wick to the emanator.

7. A cartridge according to claim 2 wherein the emanator comprises a porous material.

8. A cartridge according to claim 7 wherein the porous material is self supporting.

9. A cartridge according to claim 8 wherein the porous material is a sintered polypropylene or a sintered polyethylene.

10. A cartridge according to claim 9 wherein the surface area of the emanator is increased by including therein hollow portions, voids, slots or bores open to the atmosphere, or by otherwise providing said emanator with a convoluted surface.

11. A cartridge according to claim 2 wherein the emanator includes a formation by means of which communication is established between said emanator and the means for transporting the chemical agent.

12. A cartridge according to claim 11 wherein the chemical agent is a liquid, the means for transporting said chemical agent is a capillary device, and the formation penetrates an end portion of said capillary device when the emanator is in its first position.

13. A cartridge according to claim 12 wherein the capillary device comprises a material which is sufficiently resilient to regain, at least in part, its original shape when the emanator is moved to its second position.

14. An apparatus for emitting a volatile chemical agent which comprises:
   an integral cartridge comprising:
      a main body which includes a reservoir for the chemical agent,
      means for transporting the chemical agent to an emanator from which said chemical agent can diffuse, and
      the emanator being movably attached to the main body of the cartridge and capable of being moved between a first position in which said emanator is in communication with the means for transporting the chemical agent and a second position in which communication with said means is interrupted;
   and means for providing a flow of air over the emanator to promote diffusion of the chemical agent from said emanator.

15. An apparatus according to claim 14 in which the emanator comprises a sintered polypropylene or sintered polyethylene material whose surface area is increased by including therein hollow portions, voids, slits or bores open to the atmosphere, or by otherwise providing the emanator with a convoluted surface.

16. An apparatus according to claim 14 in which the means for providing the flow of air over the emanator is an electrically operated fan.

17. An apparatus according to claim 16 which additionally comprises a timer device whereby the fan can be caused to operated intermittently.

18. An apparatus according to claim 16 in which the main body of the integral cartridge includes:
   a first compartment comprising a reservoir for a liquid chemical agent and a first portion of a capillary device which serves as the means for transporting said chemical agent from said reservoir to the emanator, and
   a second compartment containing, or adapted to contain, electric cells for operating the fan.

* * * * *